United States Patent [19]

Randawa et al.

[11] Patent Number: 5,079,230
[45] Date of Patent: Jan. 7, 1992

[54] STABLE BIOACTIVE SOMATOTROPINS

[75] Inventors: Zafar I. Randawa; James F. Seely, both of Terre Haute, Ind.

[73] Assignee: Pitman-Moore, Inc., Lake Forest, Ill.

[21] Appl. No.: 242,542

[22] Filed: Sep. 12, 1988

[51] Int. Cl.$^5$ .................. A61K 37/36; C07K 7/10; C07K 13/00

[52] U.S. Cl. .......................... 514/12; 514/2; 514/21; 514/8; 530/399; 530/335; 530/336; 530/344; 530/324

[58] Field of Search ............. 514/2, 8, 12, 21; 530/334, 333, 324, 344, 335, 336, 399

[56] References Cited

U.S. PATENT DOCUMENTS

| | | | |
|---|---|---|---|
| 3,853,832 | 11/1974 | Li | 530/334 |
| 4,332,717 | 6/1982 | Kanaoka et al. | 260/112 |
| 4,604,359 | 8/1986 | Goeddel et al. | 435/253 |
| 4,620,948 | 11/1986 | Builder et al. | 530/419 |
| 4,766,205 | 8/1888 | Ghosh-Dastidar | 530/402 |

FOREIGN PATENT DOCUMENTS 0103395 8/1983 European Pat. Off. .
0104920 9/1983 European Pat. Off. .

*Primary Examiner*—F. T. Moezie
*Attorney, Agent, or Firm*—Wendell R. Guffey; Thomas L. Farquer

[57] ABSTRACT

The present invention provides a stable and bioactive somatotropin which has its small-loop sulfhydryl groups derivatized and a method for producing the small-loop derivatized somatotropin. The small-loop derivatized somatotoropin is stable during long term storage, i.e. it forms very few dimers, oligomers, and aggregates which inactivate the somatotropin, and has a bioactivity equal to or greater than that of the non-derivatized somatotropin.

27 Claims, No Drawings

STABLE BIOACTIVE SOMATOTROPINS

This invention relates generally to somatotropins and particularly to stable and bioactive somatotropins and methods for producing stable and bioactive somatotropins.

BACKGROUND OF THE INVENTION

The isolation, purification and properties of somatotropins are well known in the art. Generally, somatotropin, sometimes referred to as growth hormone in the art, is produced by the pituitary throughout an animal's life. Somatotropin is known to promote skeletal growth, nitrogen retention, protein synthesis and to affect glucose and lipid metabolism. Accordingly, somatotropin is recognized as a general anabolic agent.

Somatotropin can be isolated from excised pituitary tissue. See, e.g., Li, *J. Biol. Chem.* 211, 55 (1954). Somatotropin can also be obtained from genetically engineered microorganisms containing recombinant DNA which specifies the production of somatotropin. See, e.g., Seeburg, et al., *Nature,* 276, 795-798 (1978); Seeburg et al., *Nature,* 270, 486-494 (1978); Martial, *Science,* 205, 602-607 (1979); and Seeburg, et al., DNA, 2, 37-45 (1983).

Somatotropins from particular species have been studied and characterized. For example, bovine somatotropin is known to be a polypeptide synthesized in and secreted from the anterior lobe of the pituitary. A nucleotide coding sequence and an amino acid sequence of native bovine somatotropin have been reported; e.g. Miller et al., *J. Biol. Chem.,* 255, 7521-24 (1980); and Wallis, *FEBS Lett,* 35, 11-14 (1973). Bovine somatotropin is a protein of 191 amino acids and appears to be synthesized initially as a bovine pre-somatotropin of 217 amino acids; the signal sequence of 26 amino acids being removed from the N-terminal position during synthesis and secretion, e.g. Lingapa et al., *Proc. Natl. Acad. Sci. USA,* 74, 2432-36 (1977).

The preparation of bovine somatotropin is well known in the art. For example, bovine somatotropin is extracted from pituitary glands of cattle or produced via recombinant DNA technology in appropriate hosts, e.g., Miller et al., *J. Biol. Chem.,* 255, 7521-24 (1980). U.S. Pat. No. 4,443,539 to Frazier et al, discloses a process for preparing bovine somatotropin by utilizing recombinant DNA methodology to place the bovine somatotropin structural gene into yeast cells. U.S. Pat. No. 4,371,462 to Hecht, discloses a method for the purification of anterior pituitary peptides. European Patent Application Nos. 83304574.3, filed Aug. 8, 1983, with Publication Number 103,395; 82304880.6, filed Sept. 16, 1982, with Publication Number 075,444; and 81303824.7, filed Aug. 21, 1981, with Publication Number 047,600; and British Patent Application No. 2,073,245A disclose methods for producing recombinant bovine somatotropin in high yields. Strains of *E. Coli* that produce bovine somatotropin are available from the American Type Culture Collection under accession numbers ATCC 31826, 31840, 31841, 31842, and 31843.

Similarly, the preparation of natural and recombinant porcine and human somatotropin is well known. For example, in addition to the publications above which disclose methods for obtaining the porcine and human somatotropin, U.S. Pat. No. 4,604,359 discloses methods for the microbial expression of human somatotropin; U.S. Pat. No. 4,332,717 discloses methods for the purification of human somatotropin; and European Patent Application No. 83305717.7, filed Sept. 26, 1983, with Publication Number 104,920, discloses methods for producing recombinant porcine somatotropin in high yields. U.S. Pat. No. 4,604,359 discloses methods for synthesizing bioactive human somatotropin; including methods for synthesizing a bioactive tetra-S-carbamidomethyl derivative. Many other such publications and methods for various somatotropins are well known to skilled artisans, e.g. U.S. Pat. No. 4,645,755 discloses method for producing fish somatotropin.

Although methods for producing somatotropins are well known, methods for storing somatotropin during the often long period between somatotropin production and use are not well developed. Somatotropins tend to form bioinactive dimers, oligomers, and insoluble aggregates during storage. These bioinactive forms of the somatotropin lower the amount of somatotropin available for use and cause problems during administration, particularly when insoluble aggregates form precipitates in somatotropin solutions.

Methods are, therefore, needed for producing a stable and bioactive somatotropin which will not form bioinactive dimers, oligomers, and aggregates during storage.

SUMMARY OF THE INVENTION

It is, therefore, an object of the present invention to provide a stable and bioactive somatotropin which will not form bioinactive dimers, oligomers, and aggregates during storage.

It is another object of the present invention to provide a method for producing a stable and bioactive somatotropin which will not form bioinactive dimers, oligomers, and aggregates during storage.

It is a further object of the present invention to provide a composition containing a stable and bioactive somatotropin which will not form bioinactive dimers, oligomers, and aggregates during storage. The composition should be suitable for long-term storage and easy dosage preparation and administration.

These and other objects are achieved using a method which comprises selectively reducing somatotropin small-loop disulfide bonds to produce sulfhydryl groups and derivatizing the small-loop sulfhydryl groups. Derivatizing the small-loop sulfhydryl groups prevents the sulfhydryl groups from forming intramolecular disulfide bonds which cause somatotropin dimers, oligomers, and aggregates and inactivate the somatotropin. The somatotropin produced using this method is stable during long term storage and has a bioactivity equal to or greater than the bioactivity of the non-derivatized somatotropin. The derivatized somatotropin is recovered and, if needed, further processed to produce a somatotropin form suitable for long term storage and subsequent administration to an animal.

Other objects, advantages, and novel features of the present invention will become apparent from the following detailed description of the invention.

DETAILED DESCRIPTION OF THE INVENTION

Somatotropins isolated from different species of animals have a high degree of sequence homology (about 96 percent); however, somatotropins from different species do differ in the number and the sequence of amino acids present in the somatotropin chain. For example, native human somatotropin (nhST) is a polypeptide consisting of 188 amino acids. The somatotropin molecule has two disulfide bonds; one between amino acids 179 and 186 and one between amino acids 68 and 162. These disulfide bonds form a six amino acid "small-loop" and a ninety-four amino acid "large-loop", respectively. The complete sequence and structure for human somatotropin showing the "small-loop" and "large-loop" are illustrated in U.S. Pat. No. 3,853,832, incorporated herein by reference.

Similarly, native porcine somatotropin (npST) is a 190 amino acid polypeptide having two disulfide bonds forming the characteristic small-loop and large-loop; one between amino acids 180 and 188 and one between amino acids 163 and 52, respectively. Also, native bovine somatotropin (nbST) is a 191 amino acid polypeptide having two disulfide bonds forming the characteristic small-loop and large-loop; one between amino acids 181 and 189 and one between amino acids 53 and 164, respectively. Numerous synthetic and recombinant somatotropins have various numbers and sequences of amino acids. However, bioactive somatotropins have a tertiary conformation with the characteristic small-loop and large-loop.

The term "somatotropin" as used herein encompasses any somatotropins having a "small-loop" and includes not only "native somatotropins" but also "synthetic somatotropins" and "recombinant somatotropins" having the amino acid sequence of native somatotropin, amino acid sequences substantially similar thereto, or an abbreviated sequence form thereof, and their analogs and muteins having substituted, deleted, elongated, replaced, or otherwise modified sequences. In particular, somatotropin as used herein includes a recombinant protein of the same sequence as the native somatotropin, but having amino acids deleted from the amino and/or carboxy terminal end. Examples of such proteins include but are not limited to delta-7 recombinant porcine somatotropin, delta-4 recombinant bovine somatotropin, (native somatotropins having 7 and 4 residues deleted from the amino terminal end, respectively), and the like.

The term "small-loop derivatized somatotropin" as used herein describes "somatotropins" that have a large-loop formed by a disulfide bond but do not have a small-loop; the small-loop sulfhydryl groups having been derivatized to prevent the formation of the small-loop disulfide bonds. The "small-loop derivatized somatotropin" is identical in amino acid sequence to the non-derivatized "somatotropin" except for the presence of the derivatizing groups on the cysteine sulfhydryl groups which normally form the disulfide bond responsible for the small-loop.

According to the present invention, a method is provided for producing a stable and bioactive somatotropin. The method comprises selectively reducing somatotropin small-loop disulfide bonds to produce sulfhydryl groups and derivatizing the small-loop sulfhydryl groups. Derivatizing the small-loop sulfhydryl groups prevents the sulfhydryl groups from forming intramolecular disulfide bonds which cause somatotropin dimers, oligomers, and aggregates and inactivate the somatotropin. The somatotropin produced using this method is stable during long term storage and has a bioactivity equal to or greater than the bioactivity of the non-derivatized somatotropin. The derivatized somatotropin is recovered and, if needed, further processed to produce a somatotropin form suitable for long term storage and subsequent administration to an animal.

The somatotropin used herein can be obtained from any suitable source. Methods for producing, isolating and purifying native, synthetic, and recombinant somatotropins are well known in the field. Somatotropin from any animal species can be used herein; these somatotropins include but are not limited to human, bovine, porcine, canine, feline, equine, avian, piscine, and ovine somatotropins.

The somatotropin small-loop disulfide bond is selectively reduced by reacting the somatotropin with an appropriate reducing agent under conditions which reduce the small-loop disulfide bonds but do not reduce the large-loop disulfide bonds. Any suitable reducing agent which reacts with protein sulfhydryl groups can be used. Typically, the reducing agent is any organic mercapto compound represented by the formula R-SH, where R is an organic hydrocarbon radical having from about 1–30 carbon atoms. Preferred reducing agents include but are not limited to 2-mercaptoethanol and dithiothreitol.

Generally, a solution containing from about 1–20 milligrams per milliliter (mg/ml) of somatotropin is mixed with sufficient reducing agent to bring the concentration of reducing agent to from about a 15–300 millimolar (mM). The pH of the solution is adjusted to from about 6–10 and the reducing agent is allowed to react with the somatotropin for from about 0.5–3 hours at a temperature of from about 15°–50° C. Excess reducing agent is removed by any suitable means, preferably dialysis, and the resulting small-loop reduced somatotropin containing two small-loop sulfhydryl groups is derivatized as described below.

In one preferred embodiment, sufficient somatotropin is dissolved in carbonate buffer (CB−) (CB−contains 25 mM $NaCO_3$, 18 mM $Na_2CO_3$, pH about 9.5) to produce about a 5 mg/ml solution. Dithiothreitol is added in amounts sufficient to produce a 20 mM solution, the pH is adjusted to about 8, and the reduction is carried out in the dark for about 1 hour at about 37° C.

In another preferred embodiment, a CB− solution (pH of about 9.8) of about 5 mg/ml somatotropin containing 2-mercaptoethanol at a concentration of about 50 mM is reacted in the dark for about 1 hour at about 20°–37° C. The excess reducing agent is removed and the somatotropin is derivatized to form a stable and bioactive somatotropin.

The small-loop sulfhydryl groups that result from the reduction are derivatized by reacting the reduced somatotropin with an appropriate derivatizing agent. The derivatizing agent used to derivatize the small-loop reduced sulfhydryl groups can be any suitable derivatizing agent which reacts with sulfhydryl groups. Many classes of derivatizing groups which react with sulfhydryl groups are known to the skilled artisan. Examples from such classes include but are not limited to derivatizing agents such as ethylenimine, acrylonitrile, N-ethyl maleimide, 3-bromopropionic acid, 3-bromopropionamide, iodoacetamide, iodoacetic acid, N-(iodoethyl)-trifluoro-acetamide, 4-vinyl pyridine, and methyl methane thiosulfonate. Most preferably, the derivatizing agent is an alkylating agent having the formula R-X where X is a halogen, preferably I, Br or Cl, and R is an alkyl chain, branched or linear, having from about 1–30 carbon atoms, preferably from about 1–12 carbon atoms.

Generally, a 1-200 mg/ml small-loop reduced, somatotropin solution is mixed with sufficient derivatizing agent to bring the concentration of derivatizing agent to from about 50-800 millimolar (mM). The pH of the solution is adjusted to from about 6-10 and the derivatizing agent is allowed to react with the somatotropin for from about 0.5-3 hours at a temperature of from about 15°-50° C. Excess derivatizing agent is removed by any suitable means, preferably dialysis, and the resulting small-loop derivatized somatotropin containing two derivatized sulfhydryl groups is processed to produce somatotropin in a form suitable for long term storage and administration to an animal, generally a lyophilized form.

In the preferred embodiment, a CB$^-$ solution of about 5 mg/ml small-loop reduced somatotropin containing iodoacetamide at a concentration of about 200 mM at a pH of about 8.5-9 is reacted in the dark for about 1 hour at about 20°-37° C. The excess iodoacetamide is removed by dialyzing against 2% CB$^-$. The resulting derivatized somatotropin is further purified by conventional means if needed and lyophilized to produce a somatotropin which is stable during long term storage and has a bioactivity equal to or greater than that of the non-derivatized somatotropin.

According to the present invention a small-loop derivatized somatotropin is provided which is stable during long term storage and has a bioactivity equal to or greater than that of the non-derivatized somatotropin. The derivatized somatotropin differs from the non-derivatized somatotropin in that the sulfhydryl groups on the cysteines which normally form the small-loop disulfide bond have been derivatized; the sulfhydryl groups on the cysteines which normally form the large-loop disulfide bond have not been derivatized. The small-loop somatotropin therefore has a large-loop characteristic of the non-derivatized somatotropin but does not have a small-loop since the derivatized sulfhydryl groups cannot form disulfide bonds.

The small-loop derivatized somatotropin surprisingly has a bioactivity equal to or greater than that of the non-derivatized somatotropin. In addition, the small-loop somatotropin has the added advantage that it cannot form intramolecular disulfide bonds between the small-loop sulfhydryl groups which cause somatotropin dimers, oligomers, and aggregates and inactivate the somatotropin. The small-loop derivatized somatotropin is therefore more stable during long term storage.

In another aspect of the present invention, a composition comprising a mixture of small-loop derivatized somatotropin in combination with pharmaceutically acceptable carriers such as various diluents and vehicles is provided. The carrier can be any biocompatible and small-loop derivatized somatotropin compatible carrier, preferably phosphate buffered saline, Tris-HCl, arginine, histidine, and the like. Generally, any biocompatible solution or carrier with a pH between 6 and 11 would function in the present invention as a carrier for the small-loop derivatized somatotropin. The small-loop derivatized somatotropin is mixed with pharmaceutically acceptable carriers to form a composition which is stable during long term storage and allows for easy dosage preparation and administration. The composition is preferably a lyophilized form of the small-loop derivatized somatotropin and the carrier.

The invention having been generally described, the following examples are given as particular embodiments of the invention and to demonstrate the practice and advantages thereof. The recombinant porcine somatotropin (rpST) used in the examples below was produced using an *E. coli* microorganism on deposit with the American Type Culture Collection, Rockville Md., with accession No. 53031. A complete description of the microorganism is given in U.S. Pat. No. 4,656,255, incorporated herein by reference. It is understood that the examples are given by way of illustration and are not intended to limit the specification or the claims to follow in any manner.

EXAMPLE 1

Selective Reduction of Small-Loop Disulfide Bonds with 2-Mercaptoethanol

Five (5) mg/ml solutions of recombinant porcine somatotropin (rpST) in carbonate buffer (25 mM NaHCO$_3$, 18 mM Na$_2$CO$_3$, pH 9.8) were reduced for 1 hour at room temperature in the presence of 0, 30, 40, 50, 60, 70, 80, 90 and 100 mM of 2-mercaptoethanol (ME). Following reduction, each sample was reacted at room temperature in the dark for 1 hour with 200 mM iodoacetamide (IA) to derivatize sulfhydryl groups produced from the reduced cystines. The samples were analyzed by SDS-PAGE.

Analysis of the SDS-PAGE gel showed that a complete reduction of the disulfide bonds of the small-loop was achieved by incubation with 50 mM ME while the large-loop disulfide bonds remained intact. As the small-loop is reduced, there is a small (1-2 mm) decrease in mobility of rpST due to the "extension" of the C-terminal loop. Such mobility changes for cross-linked vs. uncross-linked proteins on SDS-PAGE have been reported previously, Griffith, *Biochem J.*, 126, 553-560 (1972). As more reductant is added the large-loop also becomes reduced, resulting in an even greater decrease in mobility (10-12 mm). The large-loop reduced material is essentially insoluble, since when the material reduced in >30 mM ME is centrifuged, only large-loop intact material remains in the supernatant. These results show that approximately 40-50 mM ME gives an optimal yield of small-loop reduced, carbamidomethylated rpST.

EXAMPLE 2

Selective Reduction of Small-Loop Disulfide Bonds with Dithiothreitol

Five (5) mg/ml solutions of recombinant porcine somatotropin (rpST) in carbonate buffer (25 mM NaHCO$_3$, 18 mM Na$_2$CO$_3$, pH 9.25) were reduced for 1 hour in the presence of 0, 10, 20, 30, 40, 50, 60 and 100 mM dithiothreitol (DTT) under an atmosphere of nitrogen at 37° C. Following reduction, each sample was reacted at 37° C. between pH 8.5-9.0 in the dark for 1 hour with 150 mM IA to derivatize sulfhydryl groups produced from the reduced cystines. The excess/unreacted IA was quenched with slight molar excess of DTT over IA and dialyzed overnight against 0.1 M NH$_4$HCO$_3$, pH 7.8-8.2. The dialyzed rpST was analyzed by peptide-mapping after 2 hour hydrolysis with TPCK-treated trypsin. The results are shown in Table 1.

Referring to Table 1, the data shows that a complete reduction of the disulfide bonds of the small-loop was achieved by incubation with 20 mM DTT while the large-loop disulfide bonds remained intact. This was later confirmed as shown in Example 3.

EXAMPLE 3

Characterization of Small-loop Derivatized Somatotropin

Non-derivatized rpST and small-loop derivatized rpST prepared according to the method of Example 1 were digested for two hours using trypsin. The trypsin digests were analyzed using reverse phase high pressure liquid chromatography (RP-HPLC). The results show HPLC zones with retention times of 40.4 and 98 minutes representing the small-loop and large-loop, respectively. However, after the selective reduction and carbamidomethylation of the small-loop, the HPLC zone with a retention time of 40.4 minutes completely disappeared with concomitant appearance of two zones with retention times of 3.6 and 50.9 minutes. Analyses of the new HPLC zones by automated Edman degradation confirmed that the modified rpST sample contained small-loop derivatized rpST, as predicted. The amino acid sequence data for non-derivatized and small-loop derivatized tryptic peptides are is shown in Table 2. Additional evidence for the carbamidomethylation of two cysteines of modified rpST was obtained by amino acid analysis. A value of 1.6 carboxymethyl cysteines (CMC) out of 2 for the theoretical one-loop derivatization was obtained. These data are shown in Table 3.

EXAMPLE 4

Bioactivity of the Derivatized Somatotropin

The bioactivity of non-derivatized rpST and small-loop derivatized rpST prepared according to the method of Example 1 was determined by pST binding assays using pregnant rabbit liver membranes and $^{125}$I-labelled rpST. A modified version of the assay disclosed in Tsushima et al., Radioreceptor Assay for Growth Hormone, *J. Clin. Endocrinol. Metab.*, 37:334–337 (1973) was used: The rpST sample was incubated at 30° C. for 3.5 hours with 16,000 cpm $^{125}$I-rpST. The range of concentration used for the displacement curve of the rpST standard and small-loop derivatized rpST was between 0.38–200 ng/ml. Additional information for the pST binding assay are described in Tsushima et al., Radioreceptor Assay for Growth Hormone, *J. Clin. Endocrinol. Metab.*, 37:334–337 (1973). The results show that the calculated iodine concentration at 50% (IC-50) of small-loop carbamidomethylated pST was 1.24 ng/0.5 ml equivalent of binding whereas the non-derivatized and dialyzed samples gave a value of 3.0 ng/ml and 2.9 ng/0.5 ml, respectively. The standard gave an IC$_{50}$ of 2.35 ng/0.5 ml. From these data, the percent activity of small-loop derivatized pST was calculated to be 181% as opposed to the value of about 75% for the non-derivatize somatotropin.

EXAMPLE 5

Bioactivity of the Derivatized Somatotropin

The bioactivity of non-derivatized rpST and small-loop derivatized rpST prepared according to the method of Example 1 was determined using binding activity in porcine liver membranes according to a modification of the method in Haro et al., Homologous Somatotropin Radio Receptor Assay Utilizing Recombinant Bovine Growth Hormone, *Mol. Cell Endocrinol.*, 38:109–116 (1985). The results show that the calculated IC-50 of the small loop carbamidomethylated pST was 1.29 ng/0.5 ml compared to 1.61 ng/0.5 ml for non-derivatized pST and the rpST standard. The results show that derivatized rpST had a 125% activity compared to 100% for unmodified (non-derivatized) rpST. These results show the highly unexpected finding that the somatotropins produced according to the present invention are not only more stable but are more bioactive than their unmodified precursor somatotropins.

EXAMPLE 6

Bioactivity and Biopotency of the Derivatized Somatotropin

The relative bioactivity and biopotency of non-derivatized rpST and small-loop derivatized rpST prepared according to the method of Example 1 was determined by measuring the body weight gain in hypophysectomized (hypox) rats. Four (4) groups of 10 hypox rats per group received 24 μg pST/day of pST standard, dialyzed Zn-rpST, small-loop derivatized Zn-rpST, or non-derivatized Zn-rpSt for 9 days. Rats were monitored daily and their body weight gains recorded over a 10 day period. The weight gain was measured and the percent relative bioactivity calculated as a percent of standard. The results are shown in Table 4.

Referring to Table 4, the data show that derivatized rpST produced a mean percent weight gain of 13.5% as compared to 14.4% for non-derivatized rpST. Furthermore, the data demonstrates that the carboxy-terminal small-loop is not required for somatotropin to promote growth.

EXAMPLE 7

Solution Stability of the Derivatized Somatotropin 8 mg/ml non-derivatized rpST and small-loop derivatized rpST (prepared with IA according to Example 1) solutions containing 0.5% sodium azide were prepared in either 46 mM carbonate buffer (pH 9.8) or phosphate buffered saline (pH 7.4). Aliquots of 1.25 ml were incubated in Eppendorf Microcentrifuge tubes for 0.6, 4.6, 8.8, 22 and 120 days at 37° C.

At the end of each incubation period the aliquots were removed and analyzed for rpST monomer using Superose-12 size-exclusion chromatography with a mobile phase of 46 mM carbonate buffer (pH 9.8). The relative amount of monomer, dimer and higher molecular weight aggregates formed show that there was a higher percentage of monomer recovered when the small-loop is reduced and derivatized.

EXAMPLE 8

Stability of Derivatized Somatotropin in the Wetted State

Non-derivatized rpST and small-loop derivatized rpST (prepared with IA according to Example 1) containing 5 mg/ml were dialyzed against 0.46 mM carbonate buffer an lyophilized to produce dry rpST samples for further testing. Five mg of dry small-loop derivatized and non-derivatized rpST were wetted with 0.01 ml of 50 mM Tris-HCl, pH 7.4, 0.05% sodium azide or 46 mM carbonate buffer, pH 9.8, 0.05% sodium azide. The paste was allowed to incubate for 14 days at 37° C. At the end of this time, the rpST was diluted to a final concentration of about 1.8 mg/ml in 46 mM carbonate buffer, pH 9.8, sonicated in a Branisonic 220 sonicator for several minutes, and centrifuged at 15.000×G for 5 minutes. The supernatant was analyzed for monomer content by the chromatographic procedure described in Example 6. The results show that the recovery of rpST monomer was much greater for the small-loop derivatized rpST regardless of the wetting pH, when compared with the non-derivatized rpST.

Obviously many modifications and variations of the present invention are possible in light of the above teachings. It is therefore to be understood that within the scope of the appended claims the invention may be practiced otherwise than as specifically described.

TABLE 1

Retention Behavior of Tryptic Peptides Associated with Small and Large Loops of pST

| Sample | Small Loop (RT min.) | Large Loop (RT min.) |
|---|---|---|
| Unmodified | 40.4 [T-23 + T-25] | 98.0 [T-5 + T-18] |
| Reduced (Small-Loop Only) | 3.6 [T-23], 45.0 [T-25] | 98.0 [T-5 + T-18] |
| Reduced (Small & Large Loops) | 3.6 [T-23], 45.0 [T-25] | 80.6* [T-5], 60.0 [T-18] |
| Derivatized** (Small-Loop Only) | 3.6 [T-23], 50.9 [T-25] | 98.0 [T-5 + T-18] |
| Derivatized** (Small & Large-Loops) | 3.6 [T-23], 50.9 [T-25] | 85.6 [T-5], 74.3 [T-18] |

Abbreviations used:
The retention time (RT) of each HPLC zone is given in minutes.
[T-X] = Each zone was analyzed and designated as a tryptic peptide according to position starting from amino-terminal sequence.
[T-X + T-Y] = Two tryptic peptides linked covalently by a disulfide bridge.
If unmodified pST, the small-loop consists of two tryptic peptides T-23 and T-25 which are covalently linked by a disulfide bond. Similarly, in the large-loop, T-5 and T-18 are linked.
* = The T-1 zone also elutes at this position.
** = The reduced cysteines were derivatized with IA.
Separation of 100 ug of tryptic digest of rpST was achieved by Aquapore C-8 RP-HPLC column (Brown-Lee), which was pre-equilibrated with 0.1% Trifluoroacetic acid (TFA) and eluted at 0.5 ml/min with 50% 2-Propanol in 0.1% TFA.

TABLE 2

Amino Acid Composition+ of Unmodified and Modified rpST

| AMINO ACID | UNMODIFIED SAMPLE MOLES/MOLE | MODIFIED SAMPLE MOLES/MOLE | THEORETICAL VALUE |
|---|---|---|---|
| ASP | 16.5 | 17.0 | 16 |
| THR | 7.6 | 7.7 | 8 |
| SER | 12.3 | 12.6 | 14 |
| GLU | 26.8 | 27.7 | 25 |
| PRO | 6.1 | 5.7 | 5 |
| GLY | 8.0 | 8.0 | 8 |
| ALA | 17.0 | 15.7 | 16 |
| CYS* | 3.8 | 2.4 | 4 |
| VAL | 7.6 | 5.3 | 8 |
| MET | 1.8 | 1.7 | 2 |
| ILE | 5.5 | 5.5 | 24 |
| LEU | 23.3 | 23.2 | 24 |
| TYR | 6.7 | 6.8 | 7 |
| PHE | 11.6 | 11.7 | 12 |
| LYS | 10.3 | 12.6 | 11 |
| HIS | 5.0 | 5.0 | 3 |
| ARG | 12.6 | 12.6 | 13 |
| CMC** | 0 | 1.6 | SEE CYS |
| TOTAL | 182 | 182 | 182 |

+ = Determined by amino acid analysis after 24-hour hydrolysis.
CYS* = This value was obtained as cystine and was multiplied with a factor of 2 to obtain cysteine value (expressed as moles/mole).
CMC** = Value of carboxymethyl cysteine was calculated by using appropriate standard.

TABLE 3

Amino Acid Sequence Analyses of HPLC Zones Representing Small-Loop and Carbamidomethylated T-23 Peptides (A) HPLC zone RT: 40.5 from the peptide map of Unmodified rpST.

| Cycle # | PTH-Residue | Amount (pMOL) | PTH-Residue | Amount (pMOL) |
|---|---|---|---|---|
| 1 | PHE | 609 | BLANK | — |
| 2 | VAL | 638 | ARG | 113 |
| 3 | GLU | 243 | ARG | 109 |
| 4 | SER | 223 | BLANK | — |
| 5 | SER | 154 | BLANK | — |
| 6 | CYSTINE (—S—S—) | (++)* | BLANK | — |
| 7 | ALA | 214 | BLANK | — |
| 8 | PHE | 116 | BLANK | — |
| 9 | BLANK | — | BLANK | — |

*The Cystine-PTH elutes at 14.8 minutes. The exact amount was not calculated due to non-availability of Cystine-PTH standard. Since two PTH-residues were released during 2nd & 3rd Edman cycles, it is also established that after 2 hours of hydrolysis with trypsin the carboxy-terminal Arg—Arg amino acids did not cleave. Trypsin cannot hydrolyze these bonds. It also appears that Cystine—Arg bond is resistant to trypsin hydrolysis.

(B) HPLC zone RT: 50.9 from the peptide map of Small-loop Modified rpST.

| Cycle # | PTH-Residue | Amount (pMol) |
|---|---|---|
| 1 | PHE | 114 |
| 2 | VAL | 54 |
| 3 | GLU | 44 |
| 4 | SER | ++ |
| 5 | SER | ++ |
| 6 | CAM-CYSTEINE* | (++)** |
| 7 | ALA | 56 |
| 8 | PHE | 37 |
| 9 | BLANK | — |

*The emergence of a new PTH zone at RT:9.24 is due to carbamidomethyl-cysteine.
**The amount was not calculated due to non-availability of CAM-Cys PTH standard.

TABLE 4

Bioactivity Determination of Porcine Somatotropin

| Somatotropin (ST) | Dose ug | % Weight Gain Mean | SD | % Relative Bioactivity* |
|---|---|---|---|---|
| pST Standard | 24 | 23.1** | 2.9 | 55*** |
| Dialyzed Zn-rpST | 24 | 14.4** | 2.5 | 62 |
| Small-loop derivatized Zn-RpST | 24 | 13.5** | 2.8 | 58 |
| Non-derivatized Zn-rpST | 24 | 17.1** | 2.2 | 74 |

*Relative to the pituitary derived pST standard tested at similar concentration.
**Significantly higher (P <.01) than the negative control (4.6%, Standard Deviation (SD) 3.4).
***At equivalent dose when the ST was dissolved in 9.5 high pH buffer, its relative bioactivity was 51%.

What is claimed is:

1. A method for producing a stable and bioactive somatotropin, comprising:
   selectively reducing the somatotropin small-loop disulfide bond to produce sulfhydryl groups; and
   derivatizing the small-loop sulfhydryl groups to produce a small-loop derivatized somatotropin, thereby preventing the sulfhydryl groups from forming intramolecular disulfide bonds which cause somatotropin dimers, oligomers, and aggregates and inactivate the somatotropin.

2. The method of claim 1 wherein the somatotropin is selected from the group consisting of human, bovine, porcine, canine, feline, equine, avian, and ovine somatotropins.

3. The method of claim 1 wherein the somatotropin is a recombinant somatotropin.

4. The method of claim 3 wherein the somatotropin is selected from the group consisting of human, bovine, and porcine recombinant somatotropins.

5. The method of claim 1 wherein the somatotropin small-loop disulfide bond is reduced using an organic mercapto compound represented by the formula R-SH, where R is an organic hydrocarbon radical having from about 1–30 carbon atoms.

6. The method of claim 1 wherein the somatotropin small-loop disulfide bond is reduced using a reducing agent selected from the group consisting of dithiothreitol and 2-mercaptoethanol.

7. The method of claim 1 wherein the somatotropin small-loop sulfhydryl groups are derivatized using a derivatizing agent selected from the group consisting of ethylenimine, acrylonitrile, N-ethyl maleimide, 3-bromopropionic acid, 3-bromopropionamide, iodoacetamide, iodoacetic acid, N-(iodoethyl)-trifluoroacetamide, 4-vinyl pyridine, and methyl methane thiosulfonate.

8. The method of claim 1 wherein the somatotropin small-loop sulfhydryl groups are derivatized using an alkylating agent having the formula R-X, where X is a halogen and R is an alkyl chain having form about 1-30 carbon atoms.

9. The method of claim 8 wherein X is I, Br or Cl and R is an alkyl group having from about 1-12 carbon atoms.

10. The method of claim 1 wherein the somatotropin small-loop sulfhydryl groups are derivatized using iodoacetamide.

11. A stable and bioactive somatotropin which comprises a small-loop derivatized somatotropin.

12. The somatotropin of claim 11 selected from the group consisting of human, bovine, porcine, canine, feline, equine, avian, piscine and ovine somatotropins.

13. The somatotropin of claim 11 wherein the somatotropin is a recombinant somatotropin.

14. The somatotropin of claim 13 selected from the group consisting of human, bovine, and porcine recombinant somatotropins.

15. The somatotropin of claim 11 wherein the somatotropin small-loop sulfhydryl groups are derivatized using a derivatizing agent selected from the group consisting of ethylenimine, acrylonitrile, N-ethyl maleimide, 3-bromopropionic acid, 3-bromopropionamide, iodoacetamide, iodoacetic acid, N-(iodoethyl)-trifluoroacetamide, 4-vinyl pyridine, and methyl methane thiosulfonate.

16. The somatotropin of claim 11 wherein the somatotropin small-loop sulfhydryl groups are derivatized using an alkylating agent having the formula R-X, where X is a halogen and R is an alkyl chain having from about 1-30 carbon atoms.

17. The somatotropin of claim 16 wherein X is I, Br or Cl and R is an alkyl group having from about 1-12 carbon atoms.

18. The somatotropin of claim 11 wherein the somatotropin small-loop sulfhydryl groups are derivatized using iodoacetamide.

19. A stable and bioactive somatotropin composition, comprising:
a pharmaceutically acceptable carrier; and
a small-loop derivatized somatotropin.

20. The composition of claim 19 wherein the small-loop derivatized somatotropin and carrier are lyophilized.

21. The composition of claim 19 wherein the somatotropin is selected from the group consisting of human, bovine, porcine, canine, feline, equine, avian, piscine and ovine somatotropins.

22. The composition of claim 19 wherein the somatotropin is a recombinant somatotropin.

23. The composition of claim 22 wherein the somatotropin is selected from the group consisting of human, bovine, and porcine recombinant somatotropins.

24. The composition of claim 19 wherein the somatotropin small-loop sulfhydryl groups are derivatized using a derivatizing agent selected from the group consisting of ethylenimine, acrylonitrile, N-ethyl maleimide, 3-bromopropionic acid, 3-bromopropionamide, iodoacetamide, iodoacetic acid, N-(iodoethyl)-trifluoroacetamide, 4-vinyl pyridine, and methyl methane thiosulfonate.

25. The composition of claim 19 wherein the somatotropin small-loop sulfhydryl groups are derivatized using an alkylating agent having the formula R-X, where X is a halogen and R is an alkyl chain having from about 1-30 carbon atoms.

26. The composition of claim 25 wherein X is I, Br or Cl and R is an alkyl group having from about 1-12 carbon atoms.

27. The composition of claim 19 wherein the somatotropin small-loop sulfhydryl groups are derivatized using iodoacetamide.

* * * * *